United States Patent [19]

Grakauskas et al.

[11] Patent Number: 4,594,430

[45] Date of Patent: Jun. 10, 1986

[54] SYNTHESIS OF GEMINAL DINITRO COMPOUNDS

[75] Inventors: Vytautas Grakauskas, Arcadia; Lee C. Garver; Kurt Baum, both of Pasadena, all of Calif.

[73] Assignee: United States of America as represented by the Secretary of the Air Force, Washington, D.C.

[21] Appl. No.: 696,680

[22] Filed: Jan. 31, 1985

[51] Int. Cl.$^4$ .................. C07D 305/08; C07D 333/42; C07C 79/04; C07C 79/08

[52] U.S. Cl. .......................................... 549/9; 549/28; 549/63; 549/88; 549/346; 549/424; 549/481; 549/510; 560/156; 562/553; 568/589; 568/704; 568/712; 568/926; 568/944; 260/688

[58] Field of Search ................ 560/156, 155; 568/926, 568/944, 712, 704, 307; 549/510, 346, 424, 481, 9, 28, 63, 88; 260/688; 562/553

[56] References Cited

U.S. PATENT DOCUMENTS 2,997,504  8/1961  Schecter et al. .................... 568/712
3,020,319  2/1962  Klager et al. ....................... 568/712
3,024,288  3/1962  Klager ................................. 568/712

OTHER PUBLICATIONS

Kornblum et al, J. Org. Chem., vol. 48, No. 3, pp. 332-337, 1983; "Oxidative Substitution of Nitroparaffin Salts".

Chem. and Engineering News, vol. 39, No. 24, 6/12/61, p. 44, Reaction Gives gem-Dinitro Compounds.

Matacz et al, Chem. Abstracts, vol. 96, No. 17, #142256a, "α-Dinitro Compounds", 1981.

Primary Examiner—Glennon H. Hollrah
Assistant Examiner—Dara Dinner
Attorney, Agent, or Firm—Donald S. Singer; Charles E. Bricker; William J. O'Brien

[57] ABSTRACT

Geminal dinitro compounds are prepared by reacting an organic nitro compound having a replaceable hydrogen on the carbon to which the nitro group is attached with a source of nitrite ions in the presence of an oxidizing agent and a catalytic amount of an alkali metal ferricyanide.

8 Claims, No Drawings

SYNTHESIS OF GEMINAL DINITRO COMPOUNDS

RIGHTS OF THE GOVERNMENT

The invention described herein may be manufactured and used by or for the Government of the United States for all governmental purposes without the payment of any royalty.

BACKGROUND OF THE INVENTION

This invention relates to geminal dinitro compounds and in particular to a process for preparing the same.

Many geminal dinitro compounds have found application in the production of energetic materials. 2,2-dinitropropanol (DNPOH) is useful in the production of two energetic plasticizers: bis(2,2-dinitropropyl)formal (BDNPF) and bis(2,2-dinitropropyl)acetal (BDNPA). 2,2-dinitropropanediol is useful in the synthesis of nitro-containing polymers, explosives and various other nitro-containing organic compositions.

Heretofore, the most general method for preparing α,α-dinitro compounds has been that of Shechter et al, U.S. Pat. No. 2,997,504, in which treatment of the nitronate salt of a primary or secondary nitroparaffin with silver nitrate and an inorganic nitrite in aqueous media gives the corresponding gem-dinitro compound and metallic silver. The major drawback of this method is its use of silver nitrate. Even though the metallic silver can be recovered and easily converted to silver nitrate, experience has shown that silver losses average about 1%. Such loss represents a serious economic disadvantage. Another economic disadvantage is that the process requires the use of expensive low-chloride grade sodium hydroxide to avoid formation of silver chloride.

Kornblum et al, "Oxidative Substitution of Nitroparaffin Salts", J. Org. Chem., 1983, 48, 332–337, report that in 1979 Matacz et al reported that aqueous potassium ferricyanide is a useful reagent for oxidatively substituting secondary nitroparaffin salts, but that with the salts of primary nitro compounds this reagent fails. Kornblum et al report yields of about 60 to 90% using the method of Matacz et al for the preparation of α,α-dinitro compounds, α-nitro sulfones, and α-nitro nitriles. One disadvantage of this method is the significant quantity of the ferricyanide employed. Kornblum et al employ potassium ferricyanide in amounts ranging from about 250 mol % to about 1000 mol %, based upon the amount of the nitroparrafin starting material. In a large scale process this amount of potassium ferricyanide represents a significant economic impact, even though the potassium ferricyanide is less expensive than silver and nitric acid or silver nitrate. Additionally, this amount of potassium ferricyanide represents a significant problem of disposal.

We have found that the amount of ferricyanide required for synthesis of geminal dinitro compounds can be reduced to a catalytic amount. We have also found that potassium ferricyanide can be employed as a catalyst for the synthesis of functional geminal dinitro compounds, such as alcohols and esters and also for the synthesis of terminal geminal dinitro derivatives.

Accordingly, it is an object of the present invention to provide a process for preparing geminal dinitro compounds.

It is another object of the present invention to provide a process for preparing functional geminal dinitro compounds.

Other objects, aspects and advantages of the present invention will be apparent to those skilled in the art.

SUMMARY OF THE INVENTION

In accordance with the present invention there is provided a process for producing geminal dinitro compounds which comprises reacting a nitrite salt selected from the group consisting of alkali metal nitrites and alkaline earth metal nitrites with the metal salt of an organic nitro compound of the formula

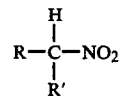

wherein R and R' each represent a substituent selected from the group consisting of hydrogen, lower alkyl, lower alkyl ether, lower alkyl carboxylic acid, and lower alkyl carbonyl compound, e.g., formaldehyde, urea, alkyl carboxylic acid ester, in the presence of an oxidizing agent and a catalytic amount of an alkali metal ferricyanide.

There is also provided a process for producing cyclic geminal dinitro compounds which comprises reacting a nitrite salt, as described above, with the metal salt of a cyclic organic nitro compound of the general formula

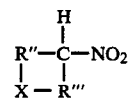

wherein X is selected from the group consisting of —O— and —S—, and R" and R'" are lower alkylene groups, in the presence of an oxidizing agent and a catalytic amount of an alkali metal ferricyanide.

DESCRIPTION OF THE INVENTION

Geminal dinitro compounds are obtained in accordance with the general reaction schemes shown below:

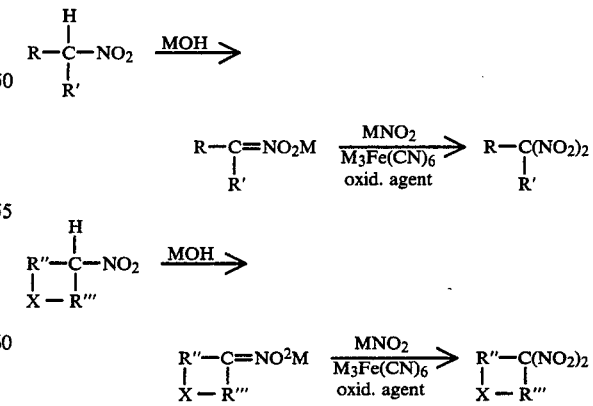

wherein M is an alkali or alkaline earth metal. The mono-nitro compound is converted to its corresponding metal salt by the action of an alkali metal or alkaline earth metal hydroxide or carbonate. The metal salt is the converted to the corresponding dinitro compound through the action of a nitrite salt in the presence of an oxidizing agent and a catalytic amount of an alkali metal ferricyanide.

The organic nitro compound may be acyclic, as given by the general formula:

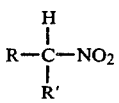

wherein R and R' are each selected from the group consisting of hydrogen, C1 to C4 alkyl, C2 to C6 alkyl ether, C2 to C4 carboxylic acid, C3 to C6 carboxylic acid ester, C6 to C9 cycloaklyl, and C7 to C9 alkaryl or aralkyl. Suitable acyclic nitro compounds include: methyl nitrate, ethylnitrate, 2.-propyl nitrate, 1-propyl nitrate, 2-nitro hexane, 5-nonyl nitrate, 2-pentyl nitrate, 2-methoxyethyl nitrate, 1-methyl-2-methoxyethyl nitrate, 3-nitropropionic acid, 2-nitropropionate, diethyl-3-nitroadipate, phenylnitromethane, and the like.

The organic nitro compound may also be alicyclic, as given by the general formula:

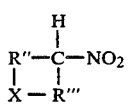

wherein X is —O— or —S—, and R" and R''' are C1-C3 alkylene groups. Examples of suitable alicyclic nitro compounds include: 3-nitrooxetane, 3-nitrotetrahydrofuran, 3-nitrothiolane, 3-nitrotetrahydropyran, 3-nitrotetrahydrothiopyran and the like.

The source of nitrite ions is any inorganic nitrite capable of furnishing nitrite ions, for example, sodium nitrite, potassium nitrite, lithium nitrite, ammonium nitrite, calcium nitrite, magnesium nitrite and the like.

The auxiliary oxidizing agent is any oxidizing agent capable of oxidizing the ferrocyanide ion to the ferricyanide ion. Suitable oxidizing agents include sodium persulfate and potassium persulfate.

Conversion of the mono-nitrate compound to the geminal dinitro compound can be carried out at a temperature between 0° C. and 100° C. Atmospheric pressure is suitable. The solvent for the reaction may be any solvent which is substantially inert to the reactants and in which the reactants are appreciably soluble. Water is preferred. The alcohols, such as for example, methanol, ethanol, ethylene glycol, etc., are satisfactory. Other solvents may also be used provided they are inert to the reactants.

In the conversion of the nitro compound to the dinitro compound, the metal hydroxide is employed in approximately equimolar amount with the nitro compound, although a slight excess of the hydroxide may be employed. The nitrite salt is employed in a ratio of about 1:1 to 5:1 moles relative to the starting quantity of nitro compound. The alkali metal ferricyanide is employed in an amount ranging from about 0.05 to 0.50, preferably about 0.10 to 0.30 moles per mole of nitro compound. The oxidizing agent is employed in an amount ranging from about 3 to about 10 moles per mole of the ferricyanide, generally about 5:1.

In the event it is desired to produce a hydroxy dinitro compound, this may be done by introducing any C1 to C5 aliphatic aldehyde, such as for example, formaldehyde, acetaldehyde, propionaldehyde, butyraldehyde, or the like into the reaction mixture. Thus, for example, nitroethane may be formylated to provide 2-nitropropanol which is then nitrated in accordance with the invention to provide 2,2-dinitropropanol. The order of these reactions can be reversed. Thus, nitroethane can be nitrated first, and the resulting 1,1-dinitroethane can then be formylated to provide 2,2-dinitropropanol.

Polynitro compounds having functional substrates can also be prepared in accordance with the invention. Nitroethers can be nitrated to the corresponding geminal dinitoethers. Cyclic nitroethers and thionitroethers can be nitrated to provide the corresponding geminal dinitro compounds. Esters of nitro carboxylic acids can be nitrated to provide the corresponding geminal dinitro esters.

A unique synthesis involving the latter substrates covers the synthesis of 3,3-dinitrobutyrolactone. 2-nitropropionic acid can be nitrated to provide 2,2-dinitropropionic acid, which is formylated to give the corresponding methylol derivative, which is then cyclized to the lactone.

The geminal dinitro compounds are useful in the production of energetic plasticizers.

The following examples illustrate the invention.

EXAMPLE 1

2,2-Dinitropropanol

To a stirred solution of 2.66 g (66.5 mmoles) of sodium hydroxide in 15 ml of water at 20° was added 5.0 g (66.5 mmoles) of nitroethane. When all the nitroethane dissolved, the solution was cooled to 5°-7° in an ice-water bath and 5.4 g of 37% aqueous formaldehyde (66.5 mmoles) was then added. The cooling bath was removed and the mixture was stirred for 2 hours before the ice-water bath was replaced and 25 ml of ether was added. A solution of 18.3 g of sodium nitrite (0.265 mole) in 30 ml of water was then added followed by solutions of 15.8 g (66.3 mmoles) of sodium persulfate in 30 ml of water and 4.4 g (13.4 mmoles) of potassium ferricyanide in 15 ml of water. The reaction temperature rose from 14° to 35°. The mixture was then stirred at ambient temperature for 1 hour and phases were separated. The aqueous phase was extracted twice with ether and the combined ether extracts were washed with brine and dried. The product was distilled in a short path distillation apparatus to give 6.57 g (65% yield) of 2,2-dinitropropanol.

EXAMPLE 2

1,1-Dinitroethane

The sodium salt of nitroethane was prepared as above. To the stirred solution was added a solution of 20 g (288 mmoles) of sodium nitrite in 50 ml of water, followed by a solution of 4.4 g (13.4 mmole) of potassium ferricyanide in 25 ml of water. Finally, 16.0 g of solid sodium persulfate (67 mmoles) was added all at once. The reaction temperature, moderated by an ice-water cooling bath, increased to 50°. The orange mixture was stirred at 25° for 1 hour and then cooled to 10°. Urea, 20 g (0.33 mole), was added, followed by 10 ml of glacial acetic acid. The mixture was extracted with three 25 ml portions of ether and the combined extracts were washed with brine and dried. The crude product was distilled to give 4.2 g (52% yield) of 1,1-dinitroethane, b.p. 87°-89° (16 mm), identified by its nmr spectrum.

A similar run using 1-nitrobutane gave an 82% yield of 1,1-dinitrobutane.

EXAMPLE 3

2,2-Dinitropropyl Formal (BDNPF)

DNPOH was prepared as described above. This time the aqueous reaction mixture was extracted with three 25 ml portions of methylene chloride instead of diethyl ether. To the dried combined extracts was added 1.0 g (11 mmoles) of s-trioxane. The resulting solution was cooled to 5° and treated with 10 ml of concentrated sulfuric acid. The mixture was stirred for two hours at ambient temperature and the phases were allowed to separate. The organic phase was washed with aqueous sodium bicarbonate, dried and concentrated to give 4.8 g of a clear and colorless oil, identified by its nmr spectrum as BDNPF. The material was contaminated with ca 5–7% of 1,1-dinitroethane which could be readily removed from the formal under reduced pressure.

EXAMPLE 4

2,2-Dinitropropanediol (A-diol)

From 2-Nitropropanediol

To a stirred solution of 400 g (6.54 moles) of nitromethane and 1050 g (13.0 moles) of 37% formalin in one liter of water was added 2 ml of a solution of 260 g (6.50 moles) of sodium hydroxide in one liter of water. The reaction temperature rose to 51° C. and then subsided to 45° C. The mixture was chilled to 8° C. and the remainder of the alkali was added dropwise at a rate to maintain the reaction temperature at 9°–10° C. A precipitate of nitronate salt formed towards the end of the addition. After 1.5 h, a solution of 1800 g (26 moles) of sodium nitrite in 2.5 l of water was added, followed by 1500 ml of tetrahydrofuran. Next, 1600 g (6.72 moles) of solid sodium persulfate was added, followed immediately by a solution of 430 g (1.3 moles) of potassium ferricyanide in 1.2 l of water. The reaction mixture was chilled in an ice-water bath and stirred vigorously as the temperature rose to 45° C. before subsiding. The mixture was cooled to 20° C., transferred to a separatory funnel, and extracted with 1.5 l of ether. The organic layer was transferred to a rotary evaporator and solvents were removed. Meanwhile, the aqueous phase was extracted with four 1.5 L portions of ether. all the extracts, including the first ether-tetrahydrofuran fraction, were combined and washed with two one-liter portions of water, followed by 500 ml of brine. The solution was dried over anhydrous magnesium sulfate and concentrated. The remaining solid was crystallized from 500 ml of methylene chloride at 0° C. to give 315 g (29% yield) of A-diol, m.p. 141°–142° C. 'H NMR(d 6- acetone): &4 40(d, 4 H, J=6 Hz,—CH$_2$O—), 5.20 (t, 2 H, J=6 Hz, —OH). 'H NMR(d$_6$-acetone, D$_2$O). & 4.40(s, 4 H, —CH$_2$O—).

Anal. Calculated for C$_3$H$_6$N$_2$O$_6$: C, 21.69; H, 3.64; N, 16.86. Found: C, 21.85; H, 3.73; N, 16.54.

From Nitromethane

To a stirred solution of 26 g (0.65 mole) of sodium hydroxide in 150 ml of water cooled at 10° was added 10 g (0.163 mole) of nitromethane. When a clear solution of nitronate salt was obtained, a solution of 45 g (0.65 mole) of sodium nitrite in 75 ml of water was added, followed by a solution of 5.5 g (17 mmoles) of potassium ferricyanide in 20 ml of water. Finally, 45 g of solid potassium persulfate was added portionwise at a rate to maintain the reaction temperature below 40°. After cooling to 25°, the ice-water bath was removed and the mixture was treated with 30 g (0.37 mole) of 37% aqueous formaldehyde and 30 ml of water. After 20 minutes, 20 ml of glacial acetic acid was added dropwise. The mixture was diluted with 100 ml of water and extracted with three 50 ml portions of ether. The combined etheral extracts were concentrated to leave a yellow oil, which was crystallized from methylene chloride to give 4.31 g (165 yield) of A-diol, identified by its NMR spectrum.

EXAMPLE 5

Methyl 2,2-Dinitrobutyrate

To a stirred solution of 40 g (0.32 mole) of sodium carbonate hydrate n 200 mL of water was added at 25° C. 10 g (68 mmoles) of methyl 2-nitrobutyrate. After 20 minutes, a solution of 23 g (0.33 mole) of sodium nitrite in 50 mL of water was added, followed by a solution of 10 g (30 mmoles) of potassium ferricyanide in 25 mL of water. Immediately thereafter, 30 g (0.125 mole) of solid sodium persulfate was added, followed by 50 mL of methylene chloride. After one hour, phases were separated and the aqueous layer was extracted with two 50 ml portions of methylene chloride. The combined methylene chloride extracts were washed with brine and dried over anhydrous magnesium sulfate. Distillation gave 6.0 g (46% yield) of product, b.p. 63°–65° C. (1.6 mm) a colorless liquid. 'H NMR indicated that the product was contaminated with ca 11% of methyl 2-nitrobutyrate, the starting material, which could not easily be removed by redistillation without a severe loss of the product. 'H NMR (CDCl$_3$): &1.25 (t, 3 H, CH$_3$). 2.75 (qt, 2 H,—CH$_2$). 3.90 (s, 3 H, CH$_3$O—).

EXAMPLE 6

3,3-Dinitro-γ-butyrolactone

To a stirred solution of 13 g (0.32 mole) of sodium hydroxide in 50 mL of water at 10° C. was added 9.3 g (78 mmoles) of 3-nitropropionic acid. After one hour, a solution of 25 g (0.36 mole) of sodium nitrite in 50 mL of water was added. Then, a solution of 5.0 g (15 mmoles) of potassium ferricyanide in 20 mL of water was then added, followed by 23 g (96 mmoles) of solid sodium persulfate. The reaction temperature was moderated by means of a cold water bath. After five minutes, 8.0 g of 37% formalin was added and the mixture was stirred for 30 minutes. Finally, 10 g of urea was added, followed by 30 mL of ether. Glacial acetic acid, 15 mL, was added dropwise. Phases were separated and the aqueous layer was extracted with three 15 mL portions of ether. The combined etheral extracts were washed with brine and dried. The solution was concentrated to give 0.95 g of amber oil, 4-hydroxy-3,3-dinitrobutyric acid. This oil was dissolved in 20 mL of benzene and ca 0.95 g of p-toluenesulfonic acid was added. The mixture was stirred at 25° C. for 17 hours and then the solution was concentrated to 10 mL and filtered. Benzene was then removed and the residual oil was crystallized from ether to give 0.20 g of a crystalline product, m.p. 100°–102° C. IR(KBr):1790 (C=O) and 1560 (NO$_2$) cm$^{-1}$. 'H NMR (d$_6$—acetone) & 4.0 (s, 2H, —CH$_2$—), 5.15 (s.2 H, —CH$_2$—).

Anal. Calculated for C$_4$H$_4$N$_2$O$_6$: C, 27.28; H, 2.29; N, 15.91. Found: C, 27.54; H, 2.16; N, 15.02.

EXAMPLE 7

2,2-Dinitropropyl Methyl Ether

A solution of 1.0 g (25 mmoles) of sodium hydroxide in 10 mL of water was treated with 2.0 g (16.8 mmoles) of 2-nitropropyl methyl ether. After 10 minutes, 10 mL of methylene chloride was added, followed by a solution of 5.0 g (72 mmoles) of sodium nitrite in 10 mL of water. Next, a solution of 1.0 g (3 mmoles) of potassium ferricyanide in 5 mL of water was added, followed by 4.4 g (18 mmoles) of solid sodium persulfate. A cold water bath was used to moderate exothermic reaction. After 30 minutes, the reaction mixture was extracted with two 15 mL portions of methylene chloride. The combined extracts were washed with brine and dried over anhydrous magnesium sulfate. The solution was distilled in a short-path distillation apparatus to give 2.43 g (88% yield) of 2,2-dinitropropyl methyl ether, a colorless liquid, b.p. 100° (16 mm). $^1$H NMR (CDCl$_3$): &2.18 (s, 3 H, —CH$_3$), 3.35 (s, 3 H, —OCH$_3$), 4.15 (s, 2H, —CH$_2$O).

EXAMPLE 8

3,3-Dinitrooxetane

A solution of 1.5 g (14.5 mmoles) of 3-nitrooxetane and 0.87 g (22 mmoles) of sodium hydroxide in 10 mL of water was stirred for 10 minute and 10 mL of methylene chloride was added. Then, a solution of 4.0 g (58 mmoles) of sodium nitrite in 10 mL of water was added, followed by 3.5 g of solid sodium persulfate and a solution of 0.96 g (2.9 mmoles) of potassium ferricyanide in 5 mL of water. A cold water bath was used to moderate the slightly exothermic reaction. After 30 minutes, the phases were separated and the aqueous layer extracted with two 30 mL portions of ether. The combined etheral extracts were washed with brine, dried and concentrated. Care was taken not to lose the very volatile product in this concentration step. The crude material was purified by sublimation at 120°–140° C. at atmospheric pressure to give 1.6 g (75% yield) of 3,3-dinitrooxetane, m.p. 70°–71° C. Its IR was identical with that of an authentic sample. $^1$H NMR (CDCl$_3$): & 5.20 (s, 4 H).

We claim:

1. A process for producing a geminal dinitro compound which comprises reacting a nitrite salt selected from the group consisting of alkali metal nitrites and alkaline earth metal nitrites with an organic nitro compound having a replaceable hydrogen atom attached to the carbon atom to which the nitro group is attached, said organic nitro compound having the general formula

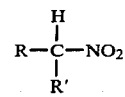

wherein R and R' are selected from the group consisting of hydrogen, C1 to C4 alkyl, C2 to C6 alkyl ether, C2 to C4 carboxylic acid, C3 to C6 carboxylic acid ester, C6 to C9 cycloalkyl, C7 to C9 alkaryl and C7 to C9 aralkyl, in the presence of an alkali metal persulfate and about 0.05 to about 0.50 moles of an alkali metal ferricyanide per mole of said organic nitro compound.

2. A process for producing a geminal dinitro compound which comprises reacting a nitrite salt selected from the group consisting of alkali metal nitrites and alkaline earth metal nitrites with an organic nitro compound having a replaceable hydrogen atom attached to the carbon atom to which the nitro group is attached, said organic nitro compound having the general formula

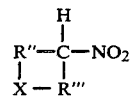

wherein X is selected from the group consisting of O and S, and wherein R'' and R''' are C1 to C3 alkylene, in the presence of an alkali metal persulfate and about 0.05 to 0.50 moles of an alkali metal ferricyanide per mole of said organic nitro compound.

3. The process of claim 1 wherein said ferricyanide is employed in an amount ranging from about 0.10 to about 0.30 moles per mole of said nitro compound.

4. The process of claim 1 wherein said nitro compound is nitroethane.

5. The process of claim 1 wherein said nitro compound is methyl 2-nitrobutyrate.

6. The process of claim 1 wherein said nitro compound is 2-nitropropyl methyl ether.

7. The process of claim 2 wherein said nitro compound is 3-nitrooxetane.

8. The process of claim 2 wherein said ferricyanide is employed in an amount ranging from about 0.10 to about 0.30 moles per mole of said nitro compound.

* * * * *